US010610353B2

(12) United States Patent
Jana et al.

(10) Patent No.: US 10,610,353 B2
(45) Date of Patent: Apr. 7, 2020

(54) METHODS FOR MAKING NANOFIBROUS COVERINGS FOR IMPLANTABLE MEDICAL DEVICES

(71) Applicant: Mayo Foundation for Medical Education and Research, Rochester, MN (US)

(72) Inventors: Soumen Jana, Rochester, MN (US); Amir Lerman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 32 days.

(21) Appl. No.: 15/845,656

(22) Filed: Dec. 18, 2017

(65) Prior Publication Data

US 2018/0221146 A1    Aug. 9, 2018

Related U.S. Application Data

(60) Provisional application No. 62/454,155, filed on Feb. 3, 2017.

(51) Int. Cl.
| | | |
|---|---|---|
| *A61F 2/24* | (2006.01) | |
| *D01D 5/00* | (2006.01) | |
| *A61F 2/82* | (2013.01) | |

(52) U.S. Cl.
CPC .......... *A61F 2/2415* (2013.01); *A61F 2/2418* (2013.01); *A61F 2/82* (2013.01); *D01D 5/0007* (2013.01); *D01D 5/0084* (2013.01); *A61F 2/2409* (2013.01); *D10B 2509/06* (2013.01)

(58) Field of Classification Search
CPC ........ A61F 2/2415; A61F 2/2418; A61F 2/82; A61F 2/2409; D01D 5/0084; D01D 5/0007; D10B 2509/06
See application file for complete search history.

(56) References Cited

U.S. PATENT DOCUMENTS

| | | | |
|---|---|---|---|
| 2009/0138067 A1* | 5/2009 | Pinchuk | A61F 2/07 623/1.13 |
| 2011/0208289 A1* | 8/2011 | Shalev | A61F 2/07 623/1.15 |
| 2014/0188212 A1* | 7/2014 | Haselby | D01D 5/003 623/1.15 |
| 2017/0325976 A1* | 11/2017 | Nguyen | A61F 2/2415 |

FOREIGN PATENT DOCUMENTS

WO    WO 2015/112839    7/2015

OTHER PUBLICATIONS

Saad et al., "Biodegradable Polymeric Materials", Encyclopedia of Materials: Science and Technology, Second Edition, pp. 551-555 , 2001. (Year: 2001).*

* cited by examiner

*Primary Examiner* — Michael N Orlando
*Assistant Examiner* — Christopher W Raimund
(74) *Attorney, Agent, or Firm* — Fish & Richardson P.C.

(57) ABSTRACT

Methods for making implantable medical devices with nanofibrous covering materials are described. For example, this document describes methods for making stent-like implantable medical devices with a skirt composed of nanofibrous material that is applied by an electrospinning process either directly or indirectly.

10 Claims, 5 Drawing Sheets

METHODS FOR MAKING NANOFIBROUS COVERINGS FOR IMPLANTABLE MEDICAL DEVICES

CROSS-REFERENCE TO RELATED APPLICATIONS

This application claims the benefit of priority to U.S. Provisional Application Ser. No. 62/454,155, filed Feb. 3, 2017. The disclosure of the prior application is considered part of (and is incorporated by reference in) the disclosure of this application.

BACKGROUND

1. Technical Field

This document relates to methods for making implantable medical devices with nanofibrous covering materials.

2. Background Information

Implantable medical devices can be deployed either percutaneously or surgically. Some implantable medical devices include a stent-like structure made of an expandable wire framework. Some such constructs are useful for prosthetic heart valve devices, stent graft devices, occluder devices, to name a few examples. Such devices may be self-expanding or expandable by external forces, such as from a balloon.

Some implantable medical devices include covering materials. For example, some prosthetic heart valve devices include one or more portions of covering materials to enhance properties such as, but not limited to, sealing and tissue ingrowth.

SUMMARY

This document describes methods for making implantable medical devices with nanofibrous covering materials. For example, this document provides methods for making implantable medical devices with a stent-like structural framework and with a skirt composed of nanofibrous material that is applied by an electrospinning process onto the structural framework.

In one implementation, a method of making an implantable medical device that comprises a structural framework and a covering material includes: (i) engaging the structural framework onto a mandrel, wherein the structural framework covers a first portion of the mandrel, and wherein a second portion of the mandrel is uncovered by the structural framework; (ii) creating the covering material by electrospinning polymer nanofibers onto at least a portion of the structural framework and onto the second portion of the mandrel such that the covering material comprises a portion formed on the structural framework and a portion formed on the second portion of the mandrel; (iii) after the electrospinning, removing the structural framework and the covering material from engagement with the mandrel; and (iv) manipulating an orientation of the covering material in relation to the structural framework such that portion formed on the second portion of the mandrel is made to directly contact the structural framework.

Such a method may optionally include one or more of the following features. The method may also include attaching the covering material to the structural framework. The attaching may include suturing the covering material to the structural framework. In some embodiments, the first portion of the mandrel does not receive the polymer nanofibers from the electrospinning. The structural framework may be a stent. In some embodiments, the implantable medical device is a prosthetic heart valve and the covering material is a skirt. The method may also include, prior to said creating the covering material, masking a portion of the structural framework using a non-conductive masking material. The non-conductive masking material may comprise tape. The covering material may be biodegradable. The covering material may be non-biodegradable.

Particular embodiments of the subject matter described in this document can be implemented to realize one or more of the following advantages. In many cases, biologic device implants benefit from recellularization/remodeling. The cell migration from body to biologic valve/device implants is necessary for recellularization/remodeling, however, cell migration can be blocked by the skirt if it is not cell-friendly and/or cellularizable. If it is cellularizable, cell will migrate to the biologic valve/device implants through the skirt or over the skirt. The skirts fabricated in accordance with the methods described herein are nanofibrous and biocompatible, so cells can grow on the skirts. In some embodiments described herein, the skirt material could be biodegradable, so the cells can grow on it, replace the skirt with cell produced biologic materials such as extracellular matrix (ECM) and further, move onto the biologic valve/device for its recellularization. In some cases, the biodegradable skirt can be replaced by cell depositing collagen fibrils and other ECM materials so that the biodegradable skirt will be changed to a fully biologic skirt. The thickness, material, mechanical properties, and porosity, etc., of the skirt can be modified according to the requirements of the particular medical device being fabricated.

In some embodiments described herein, skirts can be made from biocompatible but non-biodegradable materials. In some cases in which the skirt is made of a nanofibrous structure, endothelial cells or their progenitor cells from the blood will be deposited automatically on the surface of the skirt and there will be substantially no thrombogenic issue. In the case of some of the biodegradable skirts described herein, endothelialization will occur automatically on the newly developed biologic skirt.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes methods for making implantable medical devices with nanofibrous covering materials. In one example, this document describes methods for making stent-like implantable medical devices with a skirt composed of nanofibrous material that is applied by an electrospinning process. The techniques described herein can be readily applied for the manufacture of many other types of medical devices in addition to the particular examples provided herein. All such implementations are within the scope of this disclosure.

While the examples provided below illustrate a technique of applying a nanofibrous covering material directly onto a medical device frame, that particular technique is not required in all cases. For example, in some cases a nanofibrous covering material can be formed by an electrospinning process apart from the medical device frame and then later attached (e.g., suturing, using adhesive, etc.) to the medical device frame. In some such cases, fibers in electrospun materials could be oriented in a particular direction. In some cases, electrospun materials could have multiple layers of nanofibers with different orientations/organizations. Covering areas on one or both sides (inner and outer) of the devices can vary in accordance with the design features selected for a particular medical device.

Figure 1:
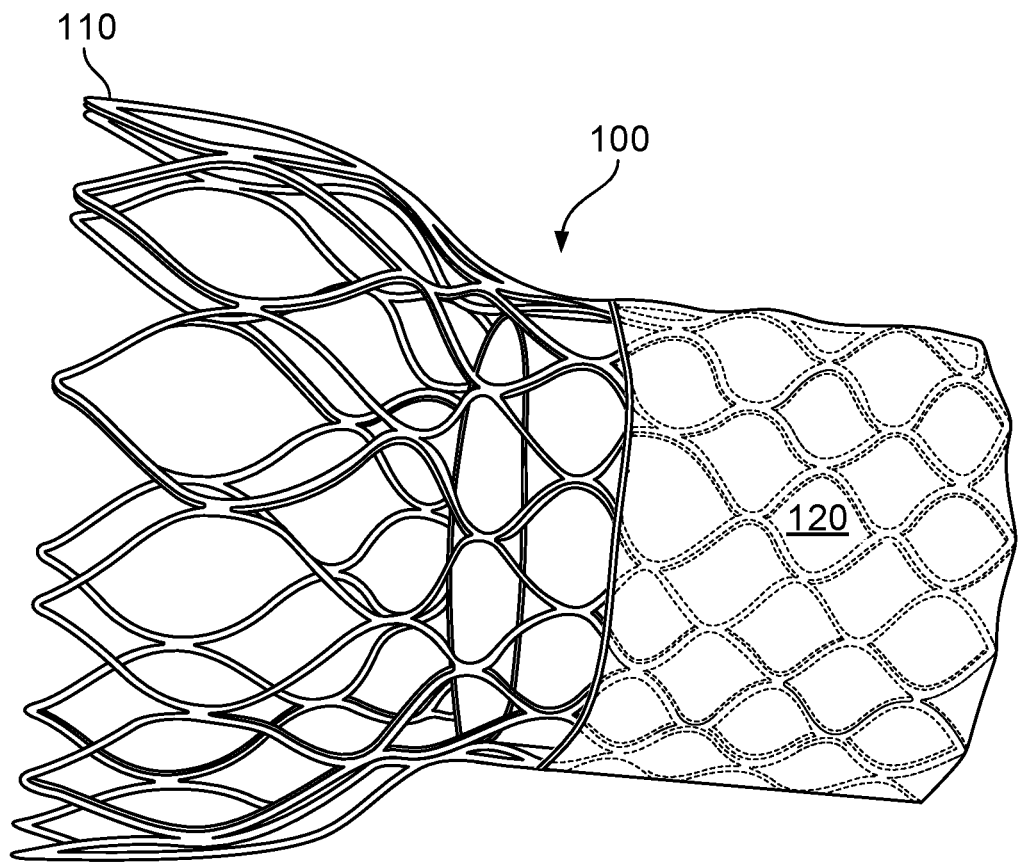
FIG. 1 is a perspective view of an example implantable medical device with a skirt material attached to a portion of the device's wire framework in accordance with some embodiments provided herein.
Figure 2:
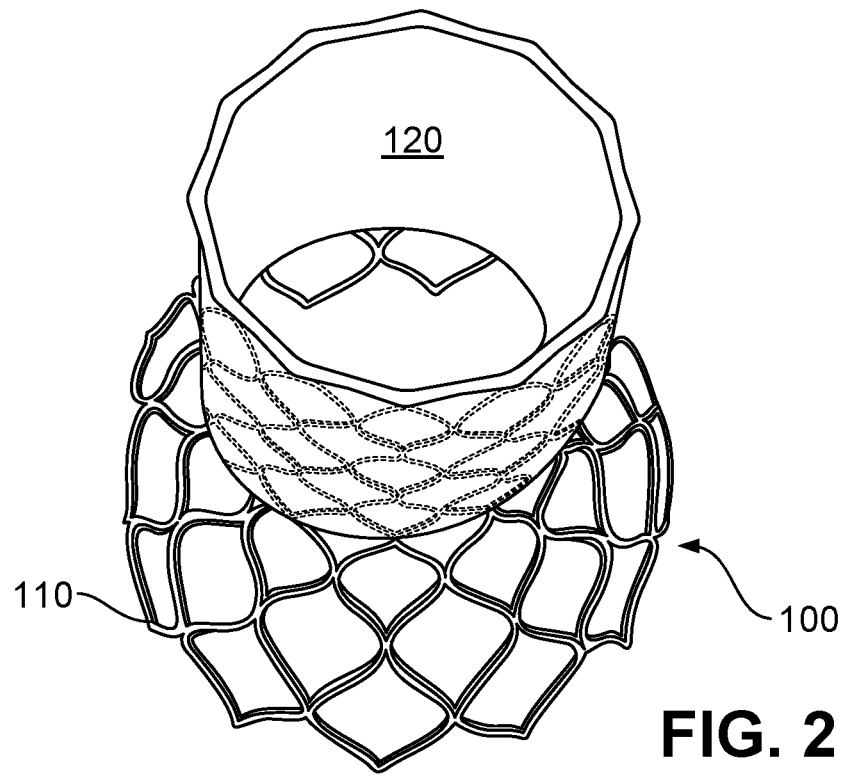
FIG. 2 is another view of the example medical device of FIG. 1.

FIGS. 1 and 2 illustrate an example medical device 100 that can be fabricated using the techniques described herein for applying a nanofibrous material using an electrospinning process. Medical device 100 includes a stent-like, wire framework 110 and a covering material 120 (which may also be referred to as a skirt 120). The techniques described herein can be used to create/apply the covering material 120 to the wire framework 110. In some cases, additional measures may be used to attach the covering material 120 to the wire framework 110. For example, in some cases suturing, using adhesives, interweaving, and the like can be used.

The covering material 120 can serve one or more medical/functional purposes depending on the characteristics that are desired for a particular type of medical device or particular usage of a medical device. For example, in some cases the covering material 120 can serve purposes such as, but not limited to, sealing against native tissue, sealing against another prosthetic member, occluding fluid flow (e.g., blood), modulating fluid flow, inhibiting endothelialization and/or tissue ingrowth, facilitating endothelialization and/or tissue ingrowth, and the like. In some embodiments, the covering material 120 is biodegradable. In some embodiments, the covering material 120 is not biodegradable. In some cases, the covering material 120 may be comprised of more than one differing types of materials. In some embodiments, the covering material 120 can receive one or more chemical treatments. Covering material 120 can be porous, non-porous, or semi-porous. The nanofibers making up the covering material 120 can be randomly arranged, or arranged in accordance with one or more patterns, or a combination thereof. Any thickness of the covering material 120 can be created using the techniques described herein. Nanofibers of various diameters can be used.

Electrospinning is a versatile technique to prepare nanofibrous substrates due to its applicability to most polymers, easy handling and cost-effectiveness. In some embodiments, the covering material 120 can be electrospun of materials such as, but not limited to, polycaprolactone, polyglycerol sebacate, poly-L-lactic acid, polyurethane, and all other biocompatible and biodegradable/non-biodegradable polymers. In some embodiments, for a biodegradable skirt, biodegradable polymer(s) such as polycaprolactone, polyglycerol sebacate, and poly-L-lactic acid can be used.

Figure 3:
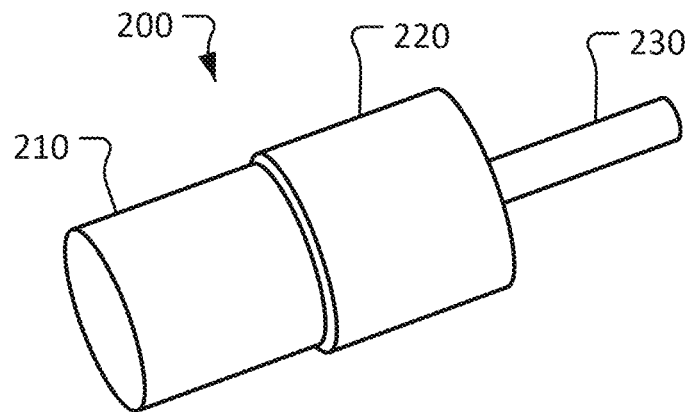
FIG. 3 is an example mandrel that can be used for making medical devices with nanofibrous coverings in accordance with some embodiments of the methods provided herein.
Figure 4:
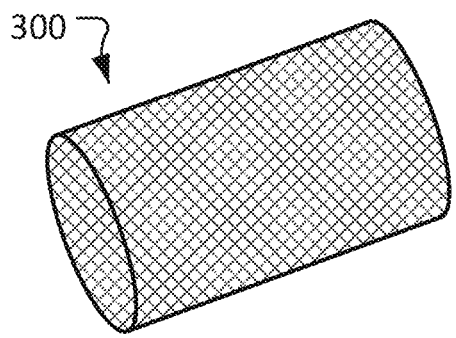
FIG. 4 is an example stent that can receive a nanofibrous covering in accordance with some embodiments of the methods provided herein.

Referring to FIG. 3, the methods for applying a nanofibrous covering to a medical device can be performed, in one example, using a mandrel 200. The mandrel 200 can be metallic (i.e., electrically-conductive stainless steel and the like) to facilitate the electrospinning process. The mandrel 200 can have any shape and form so as to be suitable for a particular medical device. In this example, the mandrel 200 is designed to receive an example cylindrical stent member 300 (as depicted in FIG. 4) on to a portion of the mandrel 200. Accordingly, mandrel 200 includes a device engagement portion 210, a mold portion 220, and a handle 230.

In the depicted example, the outer diameter of the engagement portion 210 is sized to slidably receive (e.g., using a relatively loose fit for convenience) the stent member 300. The mold portion 220 has an outer diameter that is about the same as the outer diameter of the stent member 300. In some cases, the outer diameter of the mold portion 220 may be slightly larger than the outer diameter of the stent member 300. The purpose of outer diameter of the mold portion 220 to be equal to or slightly larger than the diameter of the stent is to make the electrospun materials over mold portion 220 to be tight fit to the inner area of the stent when the electrospun materials 400 is folded within the interior of the stent member 300. In some embodiments, the mandrel 200 can be wrapped in a metallic foil prior to installing the stent member 300 onto the mandrel 200 for easy removal of the mandrel 200 from the device with its covering materials after electrospinning.

Figure 5:
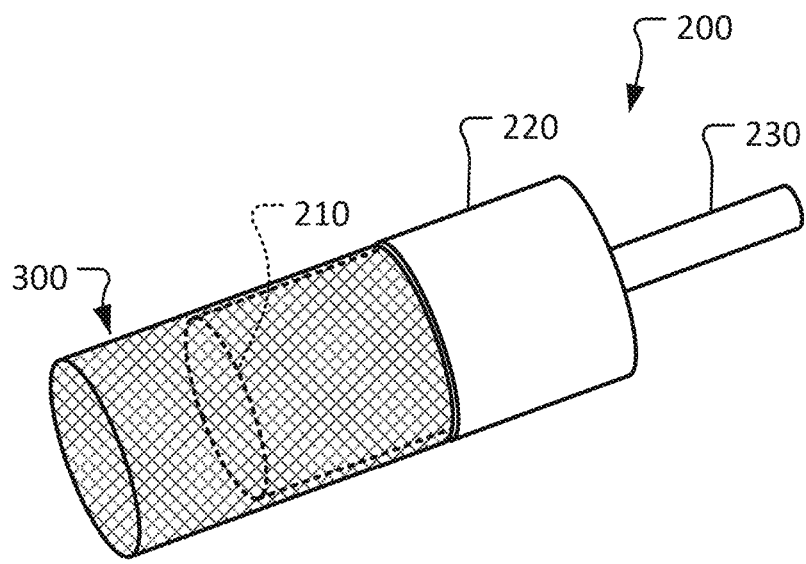
FIGS. 5-10 illustrate a series of steps for applying a nanofibrous covering to a medical device in accordance with some embodiments of the methods provided herein.

Referring also to FIG. 5, the stent member 300 can be slid onto and retained on the engagement portion 210 of the mandrel 200. In this configuration, the mold portion 220 is not covered by the stent member 300. Rather, the mold portion 220 is exposed.

Figure 6:
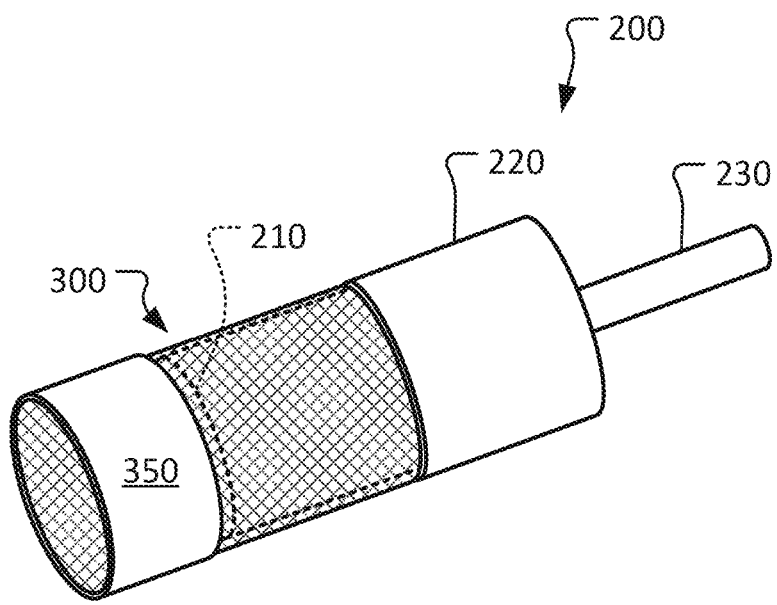

Referring also to FIG. 6, in some cases one or more portions of the stent member 300 can be masked using a non-conductive masking material 350 (e.g., using a paper tape 350) so that such portions will not receive the covering to be electrospun onto other portions of the stent member 300.

Figure 7:
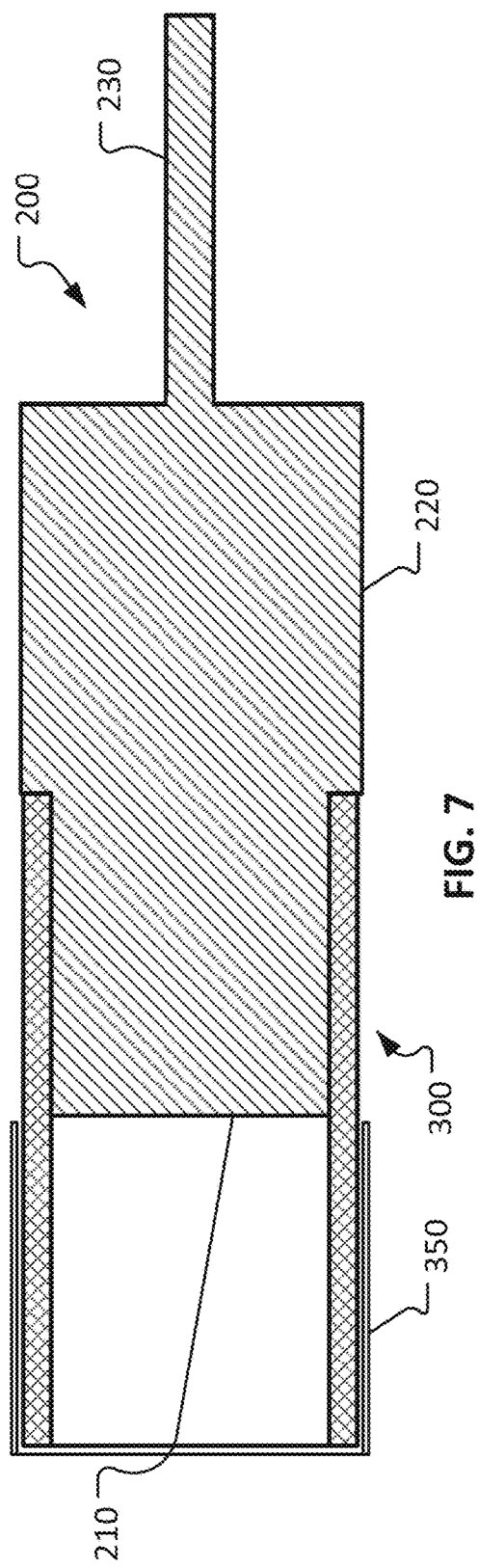

FIG. 7 shows a longitudinal cross-sectional view of the same arrangement depicted in FIG. 6. The arrangement shown is ready to receive a nanofibrous covering applied using an electrospinning process.

Figure 8:
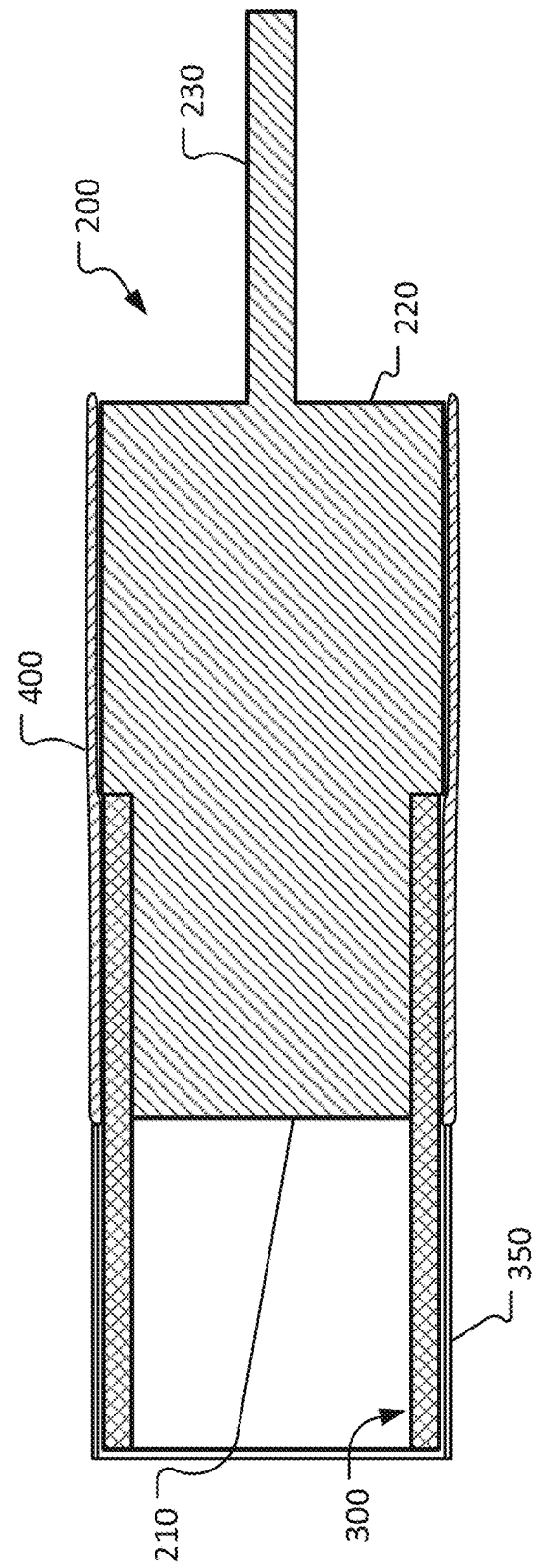

FIG. 8 depicts the same arrangement as FIG. 7, but after an electrospinning process. That is, a nanofibrous covering 400 has been applied using an electrospinning process. In this example, the nanofibrous covering 400 covers a portion of the outer diameter of the stent member 300 (that portion which is not covered by the non-conductive masking material 350) and the mold portion 220 of the mandrel 200.

Figure 9:
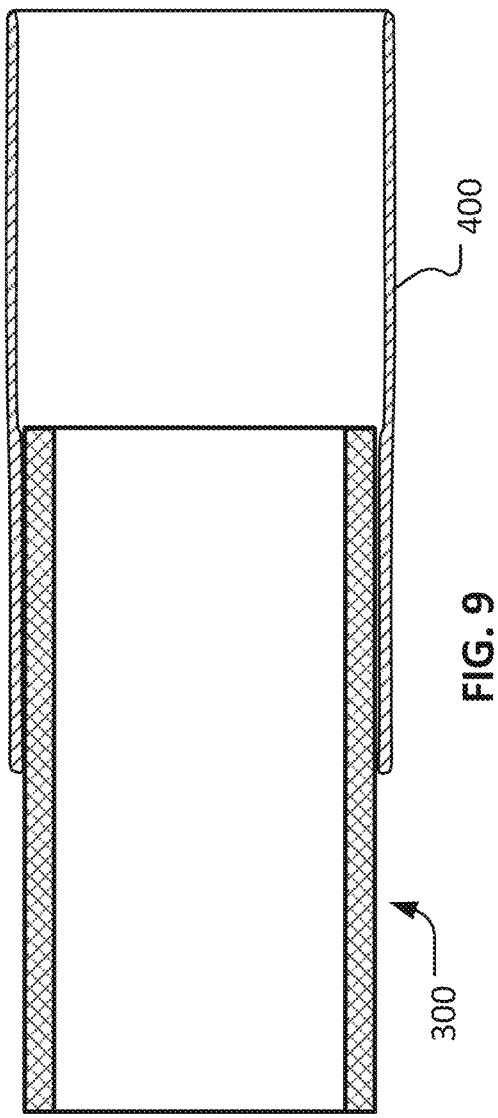

Referring also to FIG. 9, the stent member 300 and the nanofibrous covering 400 can be stripped off of the mandrel 200 or metallic foil placed before electrospinning, and the non-conductive masking material 350 can be removed from the stent member 300. It can be readily observed that the nanofibrous covering 400 is attached to a portion of the stent member 300. In addition, another portion of the nanofibrous covering 400 extends from the stent member 300 where the mold portion 220 of the mandrel 200 received the electrospun nanofibrous covering 400.

Figure 10:
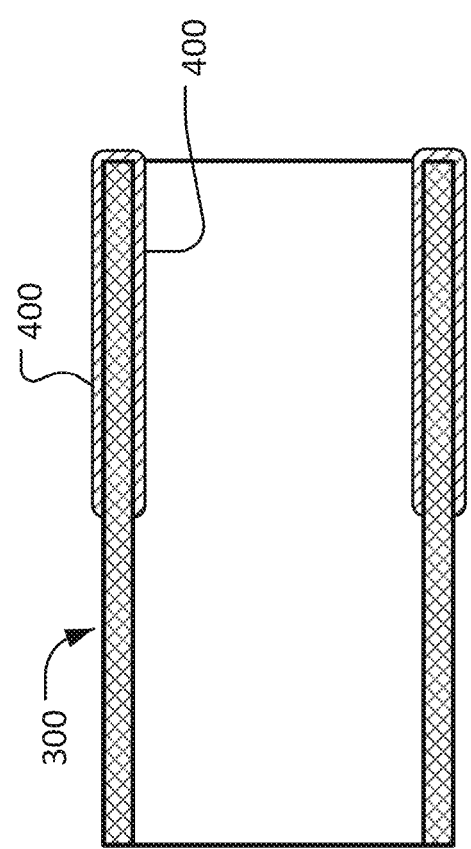

Referring to FIG. 10, the portion of the nanofibrous covering 400 extending from the stent member 300 where the mold portion 220 of the mandrel 200 received the electrospun nanofibrous covering 400 can be folded within the interior of the stent member 300. Hence, in this example both the inner surface and the outer surface of a portion of the stent member 300 are covered by the electrospun nanofibrous covering 400. At this point, in some embodiments additional attachment of the electrospun nanofibrous covering 400 to the stent member 300 can be performed. For example, in some cases both free ends of the electrospun nanofibrous covering 400 can be sutured to stent member 300 and/or to each other through the stent member 300.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of making an implantable medical device that comprises a structural framework and a covering material, the method comprising:
    engaging the structural framework onto a mandrel, wherein the structural framework covers a first portion of the mandrel, and wherein a second portion of the mandrel is uncovered by the structural framework;
    creating the covering material by electrospinning polymer nanofibers onto at least a portion of the structural framework and onto the second portion of the mandrel such that the covering material comprises a portion formed on the structural framework and a portion formed on the second portion of the mandrel, wherein the portion formed on the structural framework has a diameter that is less than or equal to a diameter of the portion formed on the second portion of the mandrel;
    after the electrospinning, removing the structural framework and the covering material from engagement with the mandrel; and
    manipulating an orientation of the covering material in relation to the structural framework such that portion formed on the second portion of the mandrel is made to directly contact the structural framework.

2. The method of claim 1, further comprising attaching the covering material to the structural framework.

3. The method of claim 2, wherein the attaching comprises suturing the covering material to the structural framework.

4. The method of claim 1, wherein the first portion of the mandrel does not receive the polymer nanofibers from the electrospinning.

5. The method of claim 1, wherein the structural framework is a stent.

6. The method of claim 5, wherein the implantable medical device is a prosthetic heart valve and the covering material is a skirt.

7. The method of claim 1, further comprising, prior to said creating the covering material, masking a portion of the structural framework using a non-conductive masking material.

8. The method of claim 7, wherein the non-conductive masking material comprises tape.

9. The method of claim 1, wherein the covering material is biodegradable.

10. The method of claim 1, wherein the covering material is non-biodegradable.

* * * * *